United States Patent

Jarvik

[11] Patent Number: 5,776,190
[45] Date of Patent: Jul. 7, 1998

[54] CANNULA PUMPS FOR TEMPORARY CARDIAC SUPPORT AND METHODS OF THEIR APPLICATION AND USE

[76] Inventor: Robert Jarvik, 124 W. 60 St., New York, N.Y. 10023

[21] Appl. No.: 325,848

[22] Filed: Oct. 19, 1994

Related U.S. Application Data

[60] Division of Ser. No. 15,246, Feb. 5, 1993, Pat. No. 5,376,114, which is a continuation-in-part of Ser. No. 969,034, Oct. 30, 1992.

[51] Int. Cl.$^6$ .................................................. A61F 2/24
[52] U.S. Cl. ............................ 623/3; 623/2; 600/16; 417/254
[58] Field of Search ........................ 623/2, 3; 604/175, 604/43; 600/16–17; 417/254–256

[56] References Cited

U.S. PATENT DOCUMENTS

| Re. 28,742 | 3/1976 | Rafferty et al. . |
|---|---|---|
| 2,635,547 | 4/1953 | Cataldo . |
| 3,608,088 | 9/1971 | Dorman et al. . |
| 3,647,324 | 3/1972 | Rafferty et al. . |
| 3,685,059 | 8/1972 | Bokros et al. . |
| 3,957,389 | 5/1976 | Rafferty et al. . |
| 3,995,617 | 12/1976 | Watkins et al. . |
| 4,037,984 | 7/1977 | Rafferty et al. . |
| 4,135,253 | 1/1979 | Reich et al. . |
| 4,173,796 | 11/1979 | Jarvik . |
| 4,382,199 | 5/1983 | Isaacson . |
| 4,507,048 | 3/1985 | Belenger et al. . |
| 4,589,822 | 5/1986 | Clausen et al. . |
| 4,625,712 | 12/1986 | Wampler . |
| 4,662,355 | 5/1987 | Pieronne et al. .............. 623/3 |
| 4,688,998 | 8/1987 | Olsen et al. . |
| 4,704,121 | 11/1987 | Moise . |
| 4,753,221 | 6/1988 | Kensey et al. . |
| 4,763,032 | 8/1988 | Bramm et al. . |
| 4,779,614 | 10/1988 | Moise . |
| 4,817,586 | 4/1989 | Wampler . |
| 4,846,152 | 7/1989 | Wampler et al. . |
| 4,895,493 | 1/1990 | Kletschka . |
| 4,898,518 | 2/1990 | Hubbard et al. . |
| 4,906,229 | 3/1990 | Wampler . |
| 4,908,012 | 3/1990 | Moise et al. . |
| 4,927,407 | 5/1990 | Dorman . |
| 4,944,722 | 7/1990 | Carriker et al. . |
| 4,955,856 | 9/1990 | Phillips . |
| 4,957,504 | 9/1990 | Chardack . |
| 4,964,864 | 10/1990 | Summers et al. . |
| 4,969,865 | 11/1990 | Hwang et al. . |
| 4,984,972 | 1/1991 | Clausen et al. . |
| 4,994,078 | 2/1991 | Jarvik . |
| 4,995,857 | 2/1991 | Arnold . |
| 5,049,134 | 9/1991 | Golding et al. . |

(List continued on next page.)

FOREIGN PATENT DOCUMENTS

| 150306 | 10/1967 | France . |
|---|---|---|
| 1514319 | 1/1968 | France . |

OTHER PUBLICATIONS

An artifical heart that doesn't beat?, JAMA, Feb. 18, 1974, vol. 227, No. 7.

*Primary Examiner*—John G. Weiss
*Assistant Examiner*—Bruce E. Snow

[57] ABSTRACT

A cannula pump is provided which incorporates a miniature rotary pump into a cardiac cannula of essentially the same size as currently utilized with routine cardiopulmonary bypass. The pump may be inserted via a single small incision in the heart to obtain both inflow and outflow cannulation simultaneously, and provide sufficient flow to completely unload the ventricle during its use. Because application of the device is extraordinarily simplified, it is suitable for rapid emergency insertion in any setting where the chest can be safely opened, including emergency room and battlefield applications. A small electric motor, implanted within the heart, provides power to the impeller via a small shaft supported on blood immersed bearings. A disposable cannula pump utilized with a reusable motor provides an inexpensive device for routine surgical use.

19 Claims, 3 Drawing Sheets

U.S. PATENT DOCUMENTS

| | | |
|---|---|---|
| 5,055,005 | 10/1991 | Kletschka . |
| 5,092,879 | 3/1992 | Jarvik . |
| 5,112,292 | 5/1992 | Hwang et al. . |
| 5,112,349 | 5/1992 | Summers et al. . |
| 5,118,264 | 6/1992 | Smith . |
| 5,145,333 | 9/1992 | Smith . |
| 5,147,388 | 9/1992 | Yamazaki . |
| 5,346,458 | 9/1994 | Affeld .......................................... 623/3 |

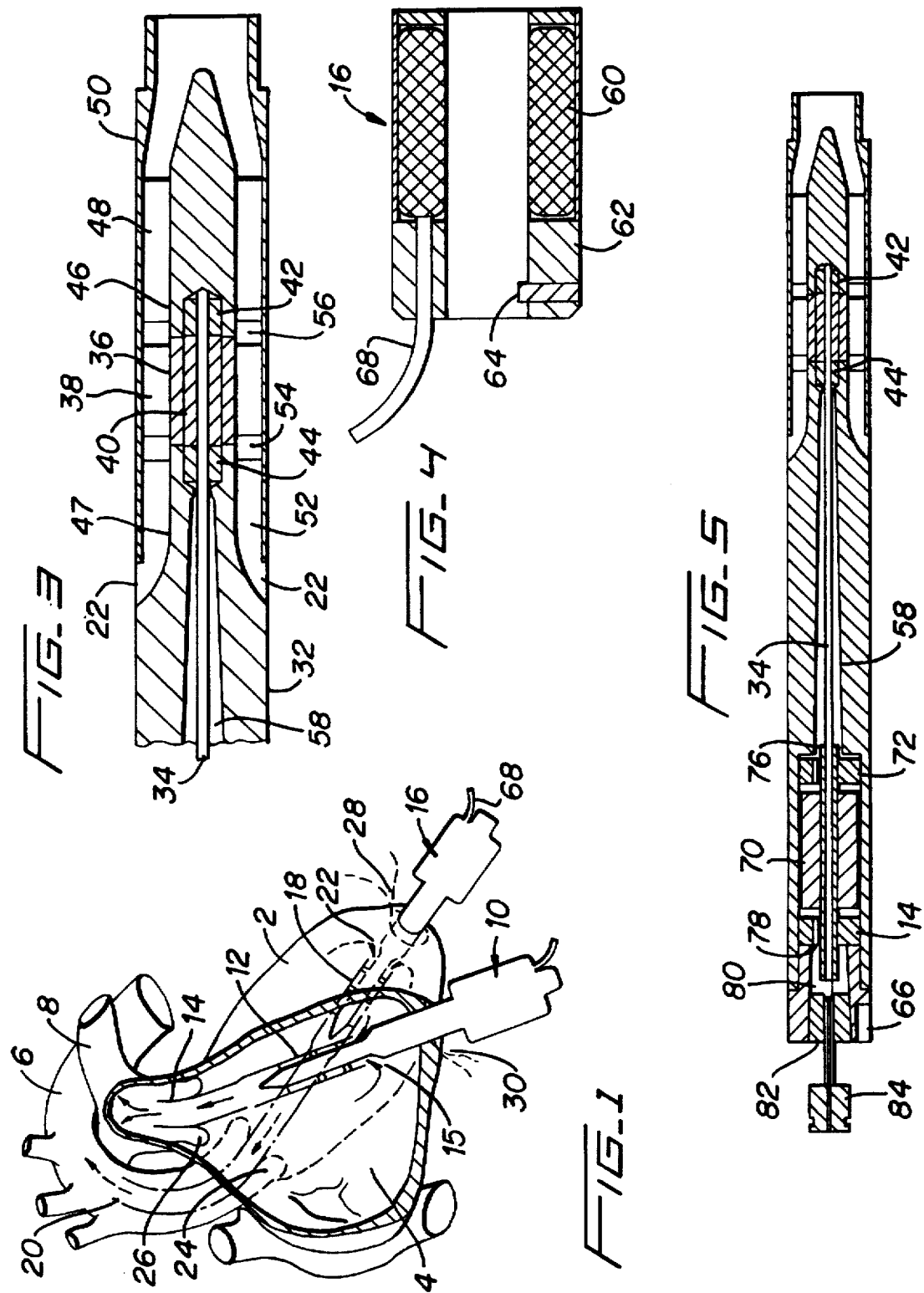

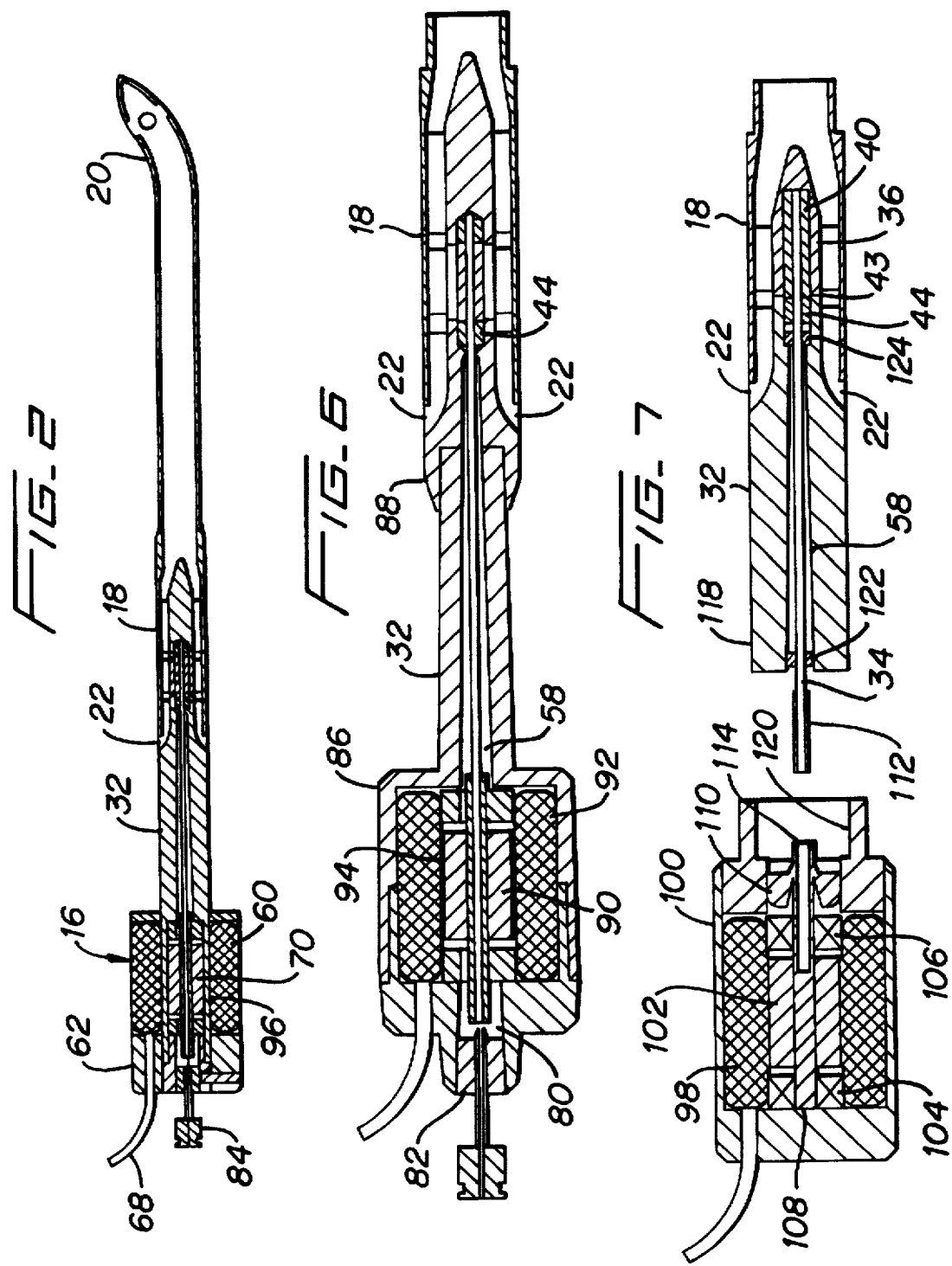

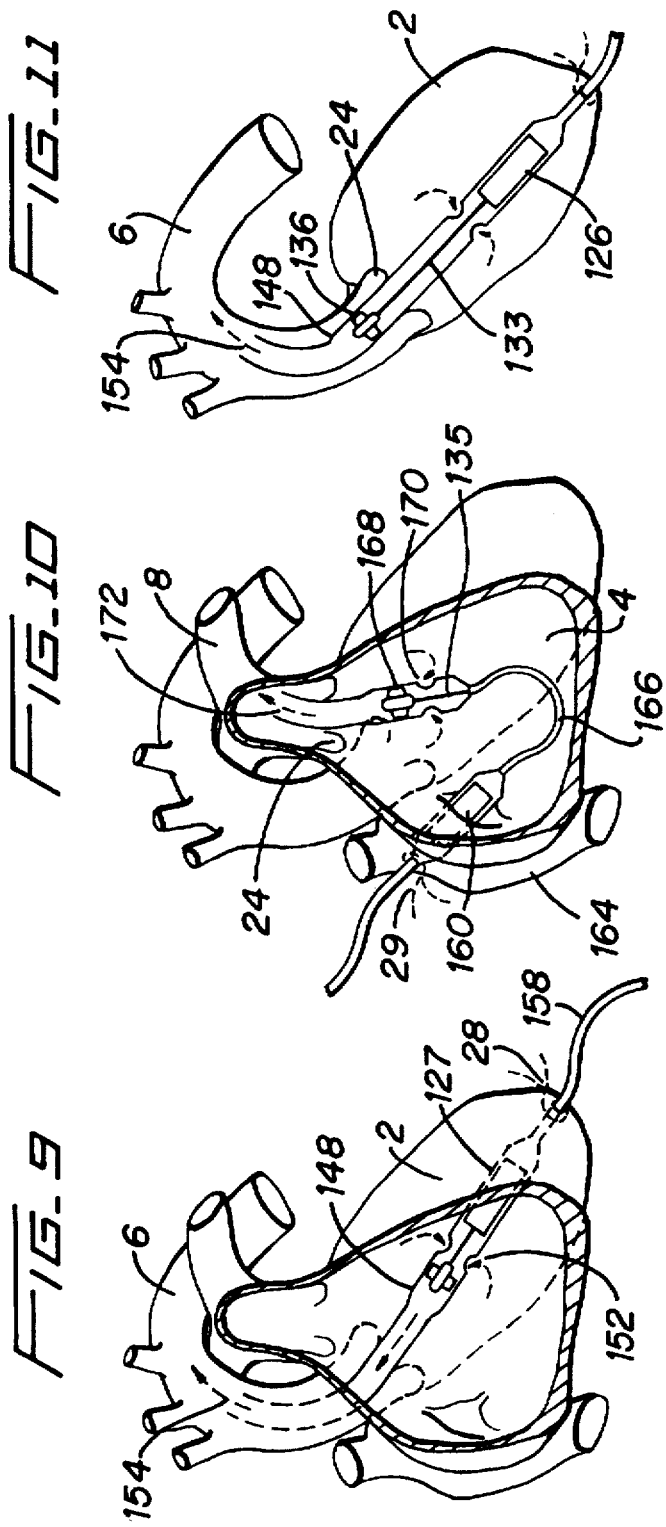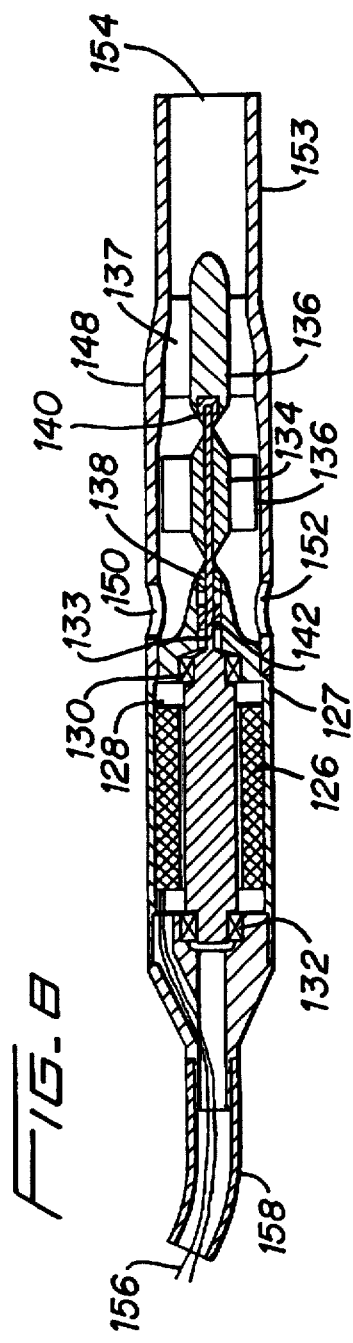

CANNULA PUMPS FOR TEMPORARY CARDIAC SUPPORT AND METHODS OF THEIR APPLICATION AND USE

This is a divisional of U.S. application Ser. No. 08/015, 246 filed Feb. 5, 1993, now U.S. Pat. No. 5,376,114, which is a continuation-in-part of U.S. application Ser. No. 07/969, 034, filed Oct. 30, 1992.

FIELD OF THE INVENTION

This invention relates to circulatory support utilizing miniature rotary blood pumps inserted into the heart for emergency use or during heart surgery. The invention includes pumps mounted within cannulae adapted for extremely simple application at surgery which are capable of providing the entire pumping output required for patient survival.

BACKGROUND OF THE INVENTION

Mechanical blood pumps are commonly applied to temporarily support the pumping function of the heart during heart surgery or during periods of heart failure. The most widely applied devices include roller pumps and centrifugal pumps currently used in more than 400,000 cases of heart surgery annually. Usually, the pumps comprise part of a cardiopulmonary bypass circuit in which many components are combined including an oxygenator, a heat exchanger, blood reservoirs and filters, and many feet of tubing to transport the blood from the patient on the operating table to the heart-lung machine located nearby and back to the patient. Blood is withdrawn from the patient via uptake cannulae placed into the vena cavae and atria or ventricles of the heart and pumped back into the pulmonary artery and aorta via return cannulae. The system generally works well but is complicated and expensive, exposes the blood to a high surface area of foreign materials which causes damage, requires full anticoagulation, and requires considerable time to set up and manage by a skilled technician.

In most cases of coronary artery bypass surgery the heart is cooled and stopped and an oxygenator is used although it is not necessary to actually open the heart as it is with valve surgery. In a few cases, the oxygenator is omitted from the system and the patients own lungs continue to function during the course of the surgical procedure. In such cases, either the pumping function of the left ventricle alone or both the left and right ventricles, is supported mechanically. Pulsatile pumps and continuous flow pumps have been used experimentally and in human cases. The heart is not cooled and is not stopped, although drugs may be given to slow its rate. The procedure has a number of important advantages in appropriate cases, however, present blood pumps, cannulae, and tubing sets have not been developed specifically for this application, and setup, cannulation, priming, and patient management during the procedure are somewhat makeshift and leave room for considerable improvement. The cannula pump of the present invention is especially suited to this use, and greatly simplifies the procedure, reducing the number of cannulation sites, reducing the surface area of foreign materials, reducing the priming volume and setup time, and permitting very simple management of heart function during the procedure.

To support the systemic circulation, a single cannula containing a miniature rotary pump is inserted into the heart, via a small incision, and both the necessary inflow and outflow connections are accomplished immediately. The blood pump may be inserted via the apex of the ventricle, the atrium, or the aorta, but in each case only one cannulation is necessary. The pump itself resides within the cannula and is connected by a short drive shaft to a small motor outside the heart, usually positioned immediately adjacent to the heart in direct connection with the cannula. If support of the pulmonic circulation is required, this is also achieved by a single cannulation via the right ventricle, right atrium, superior vena cava, or pulmonary artery. Thus, to support the total function of the heart, two cannula pumps, each requiring only one cannulation site, are used.

Cannula pumps are advantageous in cases requiring emergency circulatory support where the chest can be rapidly opened for access to the heart and the simple cannula pump can be inserted immediately. Because no cumbersome or large equipment is involved, the device can be applied in tight quarters, where use of larger more complicated systems is precluded, and in cases of cardiac arrest where there is inadequate time to setup and prime other devices. Examples include ambulance, aircraft, emergency room, cardiac cath lab, and rescue or military use in the field.

SUMMARY OF THE INVENTION

The present invention relates to miniature blood pumps utilized to provide all or part of the pumping function of the heart during cardiac surgery, during temporary periods of heart failure, and during medical emergencies involving severe heart failure. The device includes a miniature pump, such as an axialflow or mixed-flow pump mounted within a generally tubular cannula, similar in size and shape to cannulae used to withdraw blood from the heart or to return blood to the great vessels during routine heart-lung machine utilization. However, the cannulae generally differ functionally because, with the pump mounted within the cannula, a single cannula is able to provide both the inflow and outflow functions and therefore a single insertion site is sufficient, in many cases. In some cases, such as where the patient has a prosthetic valve which prevents passage of a cannula across it, two cannulation sites may be used. The pumps of the present invention may use blood-immersed mechanical bearings and the principles of high-flow washing of the junction of the rotary and stationary parts of the pump to prevent thrombus accumulation. These principles together with the method of intraventricular implantation are disclosed in my previous U.S. Pat. Nos. 4,994,078 and 5,092, 879. Although the present invention has much in common with the inventions of these prior patents, basic adaptations of the pump and motor bearing system are new as well as the cannula type of device, its function, and its methods of use. The present invention utilizes a small-diameter wire as a rotating shaft which drives the pump impeller, compared to the stationary wire of the previous devices. It is feasible for temporary use since wear is minimal in a period of a few hours or even a few weeks, compared to the permanent implant applications which require durability of many years. Tension on the wire is not required, and the wire is sufficiently stiff to impart the necessary rotary torque without warping, breaking, or vibrating excessively. The pumps are smooth and quiet during use and will not cause significant blood damage if fabricated properly.

The present invention requires major surgery for its insertion and differs from previous prior art inventions such as the "HIGH-CAPACITY INTRAVASCULAR BLOOD PUMP UTILIZING PERCUTANEOUS ACCESS" by Wampler, U.S. Pat. No. 4,625,712, in its structure and function, as well as its intended use. The present cannula pump is not suitable for percutaneous access, and is inserted via major surgery for use during the surgical procedure, or for relatively short term use following surgery. The invention of Wampler utilizes a remote motor placed about a meter away from the pump and connected to it via a long flexible shaft. The motor is located outside the body whereas the motor used with the present invention is implanted within the body and is directly coupled to the pump by a short stiff shaft only a few centimeters long. This eliminates the problem of flexible shaft breakage which has caused the FDA to withdraw experimental approval to test the Wampler pump in human patients. Since the present pump is not inserted through a long small diameter blood vessel via an access site remote from the heart, it is able to be large enough to support the entire cardiac output, as roller pumps and centrifugal pumps utilized during cardiac surgery typically must do. The Wampler pump is limited due to the small diameter mandated by the remote insertion requirement and can only provide a fraction of the blood flow necessary for full support of the patient. Essentially the Wampler pump is a remotely inserted assist pump, and the present invention is a directly inserted, high flow, total cardiac output bypass pump.

Utilizing cannula pumps of the present invention, approximately 1.2 cm in diameter, blood flow up to 8 liters per minute is obtained with 100 mm-Hg outflow pressure and rotational speed varying from approximately 15,000 to 25,000 rpm, depending upon flow and pressure. With flow in the range of 6 liters per minute and pressure in the range of 80 mm-Hg, which represents a typical operating condition, the power requirement for the system is below 15 watts. This permits battery operation for several hours with a very compact and lightweight battery. The system may include a simple control and display module which is small enough to be sterilized and utilized in the sterile surgical field. It may also incorporate microprocessor-based control and monitoring algorithms to regulate the flow and pressure, or to display the flow and pressure measured by sensors or calculated from comparison of measurements of speed and power consumption to a known database.

Cannulae may be provided with built-in pressure sensors or flow-sensing devices such as a hot-wire anemometer or ultrasonic flow probe, and may be configured such that the simple insertion of the cannulae accomplishes complete instrumentation including pressure and flow measurements at the appropriate locations. Alternatively, the cannula pumps may be used with no flow and pressure sensors and patient management can be accomplished by other observations, such as the degree of expansion or collapse of the left atrium during surgery and the adequacy of perfusion as judged by the arterial blood gases.

The cannulae pumps are capable of being fabricated utilizing primarily injection-molded, polymeric components, permitting lowcost and disposability of the cannulae and pumps themselves. The motors which provide rotary power to the shaft may be provided in a reusable configuration or also maybe made very inexpensively to permit them to be disposable. A completely disposable unit incorporating both a disposable motor and pump together with the cannulae is disclosed as one embodiment of the invention.

OBJECTS OF THE INVENTION

It is an object of the present invention to provide miniature rotary blood pumps mounted within cannulae for insertion into the heart to support its pumping function.

It is a further object of the invention to provide an extremely simple method of cardiac support capable of rapid application in medical emergencies.

It is a still further object of the invention to provide cannula pumps which can be manufactured and sold at relatively low cost, permitting routine disposable use.

It is another object of the invention to improve the art of heart surgery, improve patient care, decrease morbidity and lower hospital costs.

It is a further object of the invention to provide cannula pumps that may be rapidly and effectively applied in emergency open chest surgical procedures at remote locations away from a fully equipped hospital operating room.

It is further object of the invention to provide cannula pumps incorporating flow and pressure sensors and utilizing automatic control modes.

It is a further object of the invention to provide methods of operating the pump motor without rotary shaft seals and without the need for a continuous supply of fluid for a flush seal.

It is a further object of the invention to provide simple cannula pumps which may be coated with anticoagulants, thus avoiding or diminishing the need for systemic anticoagulation.

It is a further object of the present invention to provide a system of heart support which minimizes exposure of the blood to foreign materials.

It is an additional object of the invention to provide inexpensive disposable axial- or mixed-flow blood pumps suitable for use with an oxygenator in the system.

These and other objects of the present invention will be more fully understood by referring to the drawings and specific descriptions in the following sections.

THE DRAWINGS

Certain preferred embodiments of the invention are illustrated in the following figures:

FIG. 1 is a schematic illustration of the heart, partially in section with the anterior wall of the right ventricle and part of the pulmonary artery removed. Two cannula pumps are shown, one inserted through the apex of the left ventricle, with the out-flow across the aortic valve into the aorta and the other inserted across the apex of the right ventricle with the outflow across the pulmonic valve into the pulmonary artery.

FIG. 2 shows a longitudinal section of a cannula pump including the motor module. The pump and motor are assembled for use.

FIG. 3 is a longitudinal section of the generally cylindrical cannula and blood-pumping components contained therein. FIG. 3 is an enlarged portion of the cannula pump system illustrated in FIG. 2.

FIG. 4 is a longitudinal section of a reusable motor and motor housing. The disposable components of the cannula pump are not shown.

FIG. 5 is a longitudinal section of the disposable components the cannula pump illustrated in FIG. 2, showing all disposable components with the exception the outflow cannula and including a removable hypodermic needle for filling a fluid chamber within the device.

FIG. 6 is a longitudinal section of a cannula pump having a disposable motor disposed in a housing formed integral with the cannula.

FIG. 7 is a longitudinal section of another embodiment of a cannula pump showing a reusable motor and motor housing, and a disposable pump with the cannula in position to be coupled to the rotating shaft of the motor via a mechanical connector.

FIG. 8 is a longitudinal section of an embodiment of the invention in which a small diameter motor having an outside diameter approximately the same as the largest diameter of the pump is incorporated within the cannula.

FIG. 9 is a schematic drawing of the heart and great vessels in which a cannula pump similar to that shown in FIG. 8 has been inserted into the left ventricle with the outflow cannula section placed across the aortic valve into the aorta.

FIG. 10 is a schematic drawing of the heart showing a cannula pump placed with the electric motor in the right atrium, and the pump placed within the right ventricle, with the outflow cannula section positioned across the pulmonic valve into the pulmonary artery.

FIG. 11 is another schematic illustration showing the left ventricle and aorta, with the right ventricle removed. A cannula pump is shown placed with the motor within the left ventricle and the pump together with the outflow cannula section placed in the aorta.

GENERAL DESCRIPTION OF THE INVENTION

It is common surgical procedure to insert a tube, generally known as a cannula, into any of the various chambers of the heart or any of the great vessels which bring blood to and carry blood away from the heart. Cannulae of many sizes and shapes are used, including flexible polymer tubes, wire-reinforced polymer tubes, and even rigid metal tubes. Generally, these tubes must be small enough to permit them to be inserted into the heart or great vessels with minimal damage to the tissues and must be large enough to permit sufficient blood flow given that a considerable pressure drop occurs across small diameter tubes at higher flow rates, especially when the tubes are long. In any system where a blood pump is used to replace or assist in the function of one of the ventricles, blood must be removed via a cannula from either the ventricle itself or the inflow vessels leading to the ventricle and must then pass through a pump which ejects it into one of the large arteries.

The present invention provides pumps mounted inside the cannulae themselves which has many advantages previously cited, including greater simplicity of application to the patient, reduction in the resistance to blood flow of long tubes, reduced exposure to foreign materials, and ease of patient management. Cannula pumps may be provided in numerous embodiments, may reside within the heart itself, within the great vessels, or only a portion of the cannula may be introduced into the vascular system and the pump may be located outside the heart and beside it on the surgical field.

FIG. 1 is a generally schematic view of the heart showing two cannula pumps inserted for support of both the left heart function and the right heart function. The left ventricle, generally indicated at 2, contains a miniature axial flow pump within a cannula, and the right ventricle, indicated at 4, contains another pump. The outflow portions of the cannulae deliver blood respectively from the left ventricle 2 into the aorta 6, and from the right ventricle 4 into the pulmonary artery 8. The cannula pump in the right ventricle is driven by an electric motor, generally located and shown at 10. The actual axial flow blood pumping portion is indicated at 12, and the outflow tube which channels the blood into the pulmonary artery is shown at 14. Thus, blood enters through side holes as indicated by the arrows at 15, and directly encounters the axial flow pump hydrodynamic elements. The passage for the blood between the inflow position 15 and the outflow into the pulmonary artery, generally indicated at 14, is very short and offers both a relatively low resistance to flow and a small surface area of artificial materials to which the blood is exposed. Additionally, because the entire volume of blood within the cannula pump remains within the vascular system itself, it is appropriate to consider that the priming blood volume of this pump is essentially zero. That is, no blood need be withdrawn from the cardiovascular system to fill the pump and tubing circuit with this embodiment.

A second cannula pump, inserted in the left ventricle, is powered by an electric motor 16, and contains an axial flow pump within the left ventricle 18 into which blood enters through side holes 22 as indicated by the arrows. The blood is pumped out of the outflow portion of the cannula 20 which carries the blood across the aortic valve leaflets 24 and into the aorta 6. The right and left cannula pumps together thus intake blood from both ventricles and pump the blood into the two main arteries leaving the heart. The pump is respectively inserted through a small incision in the apex of either ventricle and held there by a purse-string suture as indicated in FIG. 1 at 30, for the right-sided cannula pump, and indicated at 28 for the left-sided pump. Since the pumps are inserted with the patient's open chest and the heart is exposed, the surgeon.can readily feel the heart and easily ascertain that the tip of the cannulae has passed across the proper valve and into the aorta or pulmonary artery as desired, rather than across an inflow valve and into the left atrium or right atrium, which would be improper. The anatomy of the heart makes proper placement relatively simple and it is almost a straight-line direct path from the apex to the aorta. With cannula pumps inserted in the fashion shown in FIG. 1, the outflow valve, that is the aortic valve or pulmonary artery valve, is able to close around the outside of the cannula permitting a sufficient seal to prevent major leakage back from the artery into the respective ventricle. This increases the effectiveness and efficiency of the pump because if the valve were absent or incompetent, a considerable portion of the blood ejected out of the cannula could flow directly back to the inflow side of the pump effectively making a short circuit without being pumped through the organs of the body as desired. However, even without complete sealing of the aortic or pulmonary artery valves, a considerable stream of blood is ejected from the cannula pump at high flow to provide momentum to the column of blood in the vessel and may provide a sort of jet-pump effect. Thus, it is possible to create a cannula pump that is functionally effective even without a cannula actually crossing the aortic or pulmonary artery valve if a sufficiently high-velocity stream of blood is ejected by the tip of a cannula pump within the ventricle and directed properly across the valve orifice.

In some patients who have mechanical heart valves implanted in either the aorta or pulmonary artery, it is not possible to pass a cannula across the mechanical valve. In such cases, cannula pumps may be used where the inflow into the pump is via the apex of the ventricle or via the atrium and the outflow of the pump returns the blood into the aorta or pulmonary artery via a second incision into that blood vessel. In certain other situations, for example in surgical procedures where the ventricular chambers of the heart must be opened for the purposes of the operation, cannula pumps that withdraw blood from the atria and return it to aorta or pulmonary artery, are required rather than devices inserted into the ventricular cavity.

FIG. 2 shows a longitudinal sectional view of the cannula pump. Blood enters the axial flow pump section 18 through side holes 22, and is ejected through the outflow cannula 20. The pump contains a rigid, relatively elongated portion 32 which is passed across the apex of the heart and serves as a support around which the heart muscle is tied utilizing the purse-string suture. An electric motor to provide power to the pump impeller is indicated at 16 and contains motor windings and laminations 60, and a housing 62 with an electric cable 68. FIG. 4 illustrates the housing containing the windings and laminations of t h e motor for use in an embodiment such as shown in FIG. 2 where the motor and housing are reusable and the other complements of the cannula pump are disposable. The motor and housing in FIG. 4 combine with the disposable pump and bearings illustrated in FIG. 5 and an outflow cannula portion to yield the complete operational device shown in FIG. 2.

Referring to FIG. 3, the general layout of an axial flow pump such as may be used with many embodiments of the invention is shown. Several axial flow pump impeller blades 38 are mounted on an impeller hub 36 supported for rotation on a set of bearings 40, 42 and 44. The impeller is driven by a stiff rotating wire 34 which transmits rotary mechanical energy produced by the electric motor to the impeller. Still referring to FIG. 3, the impeller hub rotating thrust bearing member 40 and shaft 34 are all bonded together to form a single rotating unit. Shaft 34 extends into stationary bearing 42 and is rotationally supported by it. Shaft 34 also passes through stationary bearing element 44 and is rotationally supported by that bearing member. Rotating thrust bearing member 40 is composed of a wear-resistant material similar to the stationary bearing elements 42 and 44. At each end axially it absorbs the thrust bearing load to maintain the axial position of the impeller while it is rotating and to carry and transmit thrust loads produced by the action of the impeller blades against the bloodstream. The rotating thrust bearing member 40 translates these loads to the stationary bearing members. Two small gaps 54 and 56 exist at each end of the rotating impeller hub. Blood enters these paper-thin gaps and bathes the bearings, including the small cylindrical gap between the shaft 34 and each of the stationary bearing elements 42 and 44.

The rotating impeller is supported by the bearing elements in such a fashion that there is a smooth, continuous line of flow across the junction between the stationary and rotating components of the pump at gaps 54 and 56. The blood enters the inflow side holes 22, passes across the inflow stator blades 52, supported on the inflow hub 47, smoothly crosses the gap between the inflow hub and the impeller hub at 54, passes across the impeller blades 38 and the impeller hub 36, and then smoothly passes across the gap 56 between the rotating impeller hub and outflow stator hub 46 and finally passes across the outflow stator blades 48 and then out of the pump through the outflow cannula.

FIG. 5 shows the disposable cannula pump including the axial flow pump bearings, drive shaft, and the motor magnet and motor magnet bearings utilized to transmit torque magnetically from the windings of the motor to the shaft. The elongated outflow cannula segment is omitted in FIG. 5.

A slot 66 in the disposable portion of the cannula pump is configured to receive a pin 64 (FIG. 4) as the motor is coupled to the cannula. In the embodiment shown, this coupling is accomplished by sliding the disposable cannula components shown in FIG. 5 into the motor housing shown in FIG. 4 which results in the assembly shown in FIG. 2. The pin and slot prevent the cannula from rotating within the motor housing thereby permitting the rotational torque to turn only the motor magnet and attached elements and not rotate the entire cannula. The disposable components are retained in proper connection to the reusable motor and housing components by magnetic forces, by an interference fit, or by other mechanical means.

Power to rotate the impeller is transmitted to the shaft 34 by the magnet 70 which is bonded to the shaft 34 via an intermediary hollow shaft 76. The motor magnet is caused to rotate by the rotating electromagnetic fields produced by the surrounding motor windings (60 in FIG. 2) and thus it is seen that in the embodiment shown in FIG. 5 the entire end of the disposable portion of the cannula pump containing the motor magnet may be sealed and thus eliminate rotary mechanical shaft seals through which either air or fluids could leak. The motor magnet 70 is supported by a pair of bearings 72 and 74 via the shaft 76. These bearings may be any of a number of suitable types, including fluid-lubricated sleeve-type journal bearings, ball bearings, or hydrodynamic fluid film bearings. Many materials are suitable for this application, especially considering that the cannula pump is designed for short-term use and the durability of the bearings need not be very long. Note that in the embodiment illustrated in FIG. 5, the motor magnet bearings 72 and 74 are located some distance from the pump impeller bearings 42 and 44. The drive shaft 34 transverses an elongated channel 58, and any blood which enters this chamber through the narrow gap between the shaft 34 and the impeller bearing 44 must travel the full length of this channel to reach the motor magnet bearings. A elastomeric flexible sealing stopper 82 is inserted into a hole in the end of the cannula near the motor magnet bearings. This stopper may be punctured by a small hypodermic needle 84 through which fluid can be injected into the chamber containing the motor magnet and motor magnet bearings which is in continuity with the chamber leading to the impeller bearing 44. Shortly prior to the use of the cannula pump in the patient an appropriate fluid such as sterile heparinized saline or a low-molecular-weight dextran solution is injected via hypodermic needle 84 so as to completely fill the chamber surrounding the motor magnet, motor magnet bearings, and shaft. Air that is present in this chamber at the time the fluid is ejected is forced to exit in the vicinity of the impeller through the narrow gap between the shaft 34 and the bearing sleeve 44. If sleeve-type bearings are used to support the motor magnet, such as shown in FIG. 5, a small hole 78 may be included to facilitate passage of the fluid through the bearings while the chamber is being filled. After the chamber is completely filled, the hypodermic needle is withdrawn and the stopper 82 seals the needle hole. Thereafter when the cannula pump is inserted into the heart, blood fills the outflow section of the cannula and the space surrounding the impeller and inflow and outflow stator blades and a tiny amount of blood enters the gap between the rotating impeller hub and stationary stator hubs. A film of blood diffuses into the gap between the stationary impeller bearings 42 and 44 and the rotating shaft 34. This blood mixes with the anticoagulated fluid in the gap between bearing sleeve 44 and shaft 34 and thus when the pump is turned on the bearing is immersed in blood partly diluted by the anticoagulated fluid.

In the embodiment shown in FIG. 5 there is no mechanical lip seal preventing blood from entering chamber 58 and ultimately reaching the area of the motor magnet bearings. However, since the chamber in which the motor magnet bearings are contained is rigid and sealed and pre-filled with fluid prior to use of the pump in the patient, blood cannot enter that chamber unless some of the fluid already present is removed. Therefore exchange of fluid between the bloodstream and the chamber is very limited and only a small amount of blood diffuses or seeps into the chamber during the duration of use of the cannula pump in the patient. This blood is highly diluted and anticoagulated and therefore does not interfere with the function of the motor bearings.

FIG. 6 shows an embodiment of the invention in which the electric motor as well as the remainder of the cannula pump are all integrated in one disposable unit. Disposable motor 92 is enclosed in a polymeric housing 86 which is attached to the axial flow pump section 18 at the inflow stator blade supports 88.

The embodiment shown in FIG. 6 functions very similarly to the embodiment shown in FIG. 2 and has the advantage that the air gap 94 between the motor windings 92 and the motor magnet 90 can be very small permitting high efficiency of the motor. As seen in FIG. 2, the air gap 96 must be larger when the motor is separable from the cannula parts of the pump to accommodate the cannula wall. In the configuration shown in FIG. 6, anticoagulated fluid may be injected via the hypodermic needle into chamber 80 which communicates with the elongated chamber 58 via the bore of the motor. Fluid thus can be injected via the hypodermic needle and completely fill the chambers containing the motor, motor bearings, and shaft, and reach the blood contacting portion of the pump at the impeller bearing 44.

FIG. 7 shows an additional embodiment of the invention in which the motor may be reusable and provided in a sterilizable housing which may be attached to a disposable portion of the catheter pump containing the stators, impeller, and inflow and outflow openings for the blood. Referring to FIG. 7, the motor 98 is encased in a motor housing 100 and incorporates ball bearings 104 and 106 supporting a shaft 108 fixed to the motor magnet 102. The shaft is sealed with a radial lip seal 110. The shaft has a cavity 114 which is not round in cross section but another shape such as square or rectangular and is adapted to receive a like-shaped shaft extension 112 which provides a coupling to transmit rotary torque from the motor shaft 108 to the cannula pump shaft 34. In this configuration the motor bearings and motor magnets are not surrounded by fluid but rather are surrounded by air. Blood and other fluids are kept out of the chamber in which the motor is housed by the rotary shaft seal 110. Similarly, chamber 58 in the disposable part of the device may remain filled with air rather than fluid because two rotary shaft seals 122 and 124 are utilized to exclude fluids. Thus, prior to operation of the embodiment shown in FIG. 7, the cannula portion is affixed to the motor portion by inserting the shaft 112 into the hole 114 and pressing the end of the cannula 118 into the hole 120 in the end of the motor housing. The parts may be thus attached together by an interference friction fit or other methods of retention may be provided, such as a screw-on connector. The function of the blood pump impeller, stators, and pump impeller bearings is very similar to that described for the embodiment shown in FIG. 3, with the bearings immersed in blood which enters the narrow gaps between the rotating and stationary parts.

FIG. 8 illustrates a cannula pump in which a motor 126 is utilized which is of small enough diameter to be inserted through a small incision in the heart, such as in the apex. Such a motor, approximately 12 mm in diameter by 22 mm long, provides sufficient power to pump the entire normal workload of the left ventricle, and sufficiently powerful motors can be made even smaller. The motor receives electric power through wires 156 which enter the heart via a cable 158 which passes across the wall of the ventricle and is sealed by a purse string suture 28 or may pass across the wall of the heart at another location. The rotor of the motor 128 is supported by bearings 130 and 132 and is connected to the pump impeller hub 134 which supports the impeller blades 136 by a small diameter shaft 133. In the present embodiment, a rotary shaft seal 142 prevents blood from entering the motor and motor bearing housing 127. Additional blood immersed bearings, 138 and 140 are provided to support the shaft within the blood stream. Bearing 138 is supported in the motor housing and bearing 140 is supported by the hub of the outflow stator 136 which in turn is supported by outflow stator blades 137 within the pump housing 148. Thus, when power is applied to rotate the motor rotor the rotary mechanical power it provides is transferred to the impeller via the rotating shaft 133, the action of the rotor blades against the blood draws blood into the pump via inflow openings 150 and 152 and pumps the blood through the outflow cannula 153 and out of the outflow opening 154.

FIG. 9 shows a cannula pump inserted into the left ventricle 2 at the apex and retained in place temporarily by a purse string suture 128. The power cable 158 protrudes from the apex and connects to the motor controller and electric power source (not shown). This embodiment is advantageous compared to that shown in FIG. 1 in which the motor located outside the heart can interfere with the surgeon's other tasks, such as suturing coronary artery bypass grafts.

FIG. 10 shows another embodiment in which the device is inserted across the wall of the right atrium and affixed in place by a purse string suture 29. The device utilizes a motor 160 which is within the right atrium 164, connected to the rump impeller, 168 by a flexible shaft 166 and also a small diameter rigid shaft 135. This shaft is supported on blood immersed bearings (not shown) in a fashion similar to the pump of FIG. 8. The pump is enclosed in a pump housing 170 which is located in the left ventricle and the blood is pumped across an outflow cannula through the aortic valve 24 and is discharged into the aorta at 172. This separation of the motor and pump has the advantage that there is a long distance for blood to diffuse from the pump to the motor for embodiments that do not use a rotary shaft seal. Similarly, an embodiment similar to that shown in FIG. 10 can be applied with the motor in the left atrium and the pump in the left ventricle.

FIG. 11 shows another embodiment similar to that shown in FIG. 8 in which the pump housing 148 is elongated sufficiently to permit the pump 136 to be in the aorta while the motor 126 is in the ventricle. The rotating shaft 133 transmits power across the aortic valve 24 to the pump impeller.

Additional embodiments of the cannula pump invention include embodiments in which the cannula pump is provided with two separate flexible polymeric tubular extensions to permit insertion of one as an inflow and the other as an outflow tube. Thus without departing from the scope of the above defined invention, numerous other useful embodiments may be provided.

The information disclosed in the description of the present invention is intended to be representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention which as a matter of language might be said to fall there between.

I claim:

1. A method for supporting all or part of the pumping function of a heart, comprising the steps of:
   a) providing a cannula pump including a cannula housing having a pump section and a motor section, the pump section having a pumping mechanism, the motor section having an electric motor mounted therein for imparting movement to the pumping mechanism, the pump section and motor section having substantially equal outer diameters, the cannula housing further including at least one blood inflow opening disposed in the pump section to permit blood to enter the pump section and at least one blood outflow opening to permit blood to exit the cannula housing;
   b) positioning the cannula pump within one of the left and right ventricles of a patient's heart such that at least the electric motor is contained within the one ventricle and the outflow opening of the cannula housing is disposed within a respective artery associated with the one ventricle; and
   c) activating the electric motor such that the pumping mechanism directs blood entering through the inflow opening of the cannula housing through the outflow opening of the cannula housing.

2. The method of claim 1, wherein the step of activating the electric motor includes rotating an impeller of the pump mechanism such that the impeller imparts mechanical energy to blood within the cannula housing to direct the blood through the outflow opening of the cannula housing.

3. The method of claim 2, wherein the step of providing a cannula pump includes providing a rotary pump selected from the group consisting of axial flow, mixed flow and centrifugal pumps.

4. The method of claim 2, wherein the step of activating the electric motor actuates a magnetically actuated rotatable rotor of the electric motor to cause rotation of the impeller.

5. The method of claim 4, wherein the step of actuating the electric motor rotates a rotatable drive shaft operatively connected to the rotor to thereby cause rotation of the impeller.

6. The method of claim 1, wherein the step of positioning the cannula pump includes positioning an impeller of the pumping mechanism within the one ventricle.

7. The method of claim 6, further comprising the step of making a small incision in the apex of one of the left and right ventricles and the step of positioning the cannula pump includes the step of inserting the cannula pump through the small incision.

8. The method of claim 1, further including the step of making an incision in the patient's heart in the one ventricle to permit positioning of the cannula pump at least partially within the one ventricle, the step of making an incision in the patient's heart being performed prior to the step of positioning the cannula pump.

9. The method of claim 8, wherein the step of making an incision includes the step of making a small incision in the apex of the heart.

10. The method of claim 8, wherein the step of positioning the cannula pump includes introducing a constricted portion of the cannula housing within the incision made in the heart to at least partially position the cannula pump within the one ventricle.

11. The method of claim 1, wherein the step of positioning the cannula pump includes positioning a constricted portion of the cannula housing within a respective artery associated with the one ventricle, the constricted portion defining the outflow opening.

12. The method of claim 1, wherein the step of activating the electric motor causes the pump to direct blood entering through at least one inflow opening formed in a side wall of the cannula housing.

13. The method of claim 12, wherein the step of providing a cannula pump includes providing the cannula housing with a plurality of openings in the side wall.

14. The method of claim 1, further comprising positioning a second cannula pump at least partially within the other of the ventricles of the patient's heart.

15. The method of claim 14, further comprising the step of activating an electric motor of the second cannula pump to direct blood through an outflow opening of the pump, the electric motor being positioned in the ventricle.

16. A method for supporting all or part of the pumping function of a heart, comprising the steps of:
   providing a cannula pump including a cannula housing having a pump section and a motor section, the pump section having a pumping mechanism, the motor section having an electric motor mounted therein for imparting movement to the pumping mechanism, the pump section and motor section having substantially equal outer diameters, the cannula housing further including at least one blood inflow opening disposed in the pump section to permit blood to enter the pump section and at least one blood outflow opening to permit blood to exit the cannula housing;
   b) positioning the cannula pump within one of the left and right ventricles of a patient's heart such that at least the electric motor is contained within the one ventricle and an impeller of the pump mechanism is at least partially within an artery associated with the one ventricle; and
   c) activating the electric motor such that the pumping mechanism directs blood entering through the inflow opening of the cannula housing through the outflow opening of the cannula housing.

17. A method for supporting all or part of the pumping function of a patient's heart, comprising the steps of:
   a) providing a cannula pump including a cannula housing having at least one blood inflow opening in a side wall of the cannula housing and an outflow opening, a pump mechanism disposed within the cannula housing and having an impeller mounted for rotational movement, an electric motor disposed within the cannula housing and having a magnetically actuated rotor, and a rotatable drive shaft operatively connected to the rotor and operatively connected to the impeller such that rotational movement of the rotor causes corresponding rotational movement of the impeller;
   b) making an incision in the heart adjacent one of the left and right ventricles;
   c) inserting the cannula pump within the incision such that the impeller and the electric motor are contained within the one ventricle and the outflow opening is disposed within an artery associated with the one ventricle; and
   d) activating the electric motor such that the impeller imparts mechanical energy to the blood entering the inflow opening to direct the blood through the outflow opening.

18. The method of claim 17, wherein the step of making an incision includes the step of making a small incision in the apex of the heart.

19. The method of claim 17, wherein the step of inserting the cannula pump includes initially inserting a constricted portion of the cannula housing within the incision in the heart to at least partially position the cannula pump within the one ventricle.

* * * * *